United States Patent [19]

Neuburger et al.

[11] Patent Number: 5,256,574
[45] Date of Patent: Oct. 26, 1993

[54] METHOD FOR SELECTIVE DETECTION OF LIQUID PHASE HYDROCARBONS

[75] Inventors: Glen G. Neuburger, Jackson; Paul C. Warren, Far Hills, both of N.J.

[73] Assignee: Bell Communications Research, Inc., Livingston, N.J.

[21] Appl. No.: 866,615

[22] Filed: Apr. 10, 1992

Related U.S. Application Data

[60] Division of Ser. No. 584,894, Sep. 20, 1990, which is a continuation-in-part of Ser. No. 371,542, Jun. 26, 1989, abandoned.

[51] Int. Cl.$^5$ ............................................. G01N 27/12
[52] U.S. Cl. .................................... 436/143; 436/131; 436/132; 436/142; 436/151; 73/313
[58] Field of Search ................................ 436/139–143, 436/149, 151, 131, 132; 338/13, 34; 73/313, 40, 61.43

[56] References Cited

U.S. PATENT DOCUMENTS

| | | | |
|---|---|---|---|
| 4,631,952 | 12/1986 | Donaghey | 422/98 X |
| 4,639,711 | 7/1987 | Edholm et al. | 338/114 |
| 4,818,439 | 4/1989 | Blackledge et al. | 252/511 |
| 4,855,706 | 8/1989 | Hauptly | 338/34 |
| 4,926,165 | 5/1990 | Lahlouh et al. | 73/40 X |
| 5,070,944 | 1/1992 | Boenning et al. | 72/23.4 |
| 5,101,657 | 4/1992 | Lahlouh et al. | 73/40 |

Primary Examiner—James C. Housel
Assistant Examiner—Jeffrey R. Snay
Attorney, Agent, or Firm—Leonard Charles Suchyta; Lionel N. White

[57] ABSTRACT

A method for the selective detection of liquid phase hydrocarbons in the $C_6$–$C_{16}$ range includes a matrix comprising a silicone polymer having dispersed therein a conductive carbon black filler of high structure and comprises signaling the presence of hydrocarbon liquid phase when the electrical resistivity of the sensor increases to a preselected threshold level intermediate the vapor and liquid phase resistivities.

1 Claim, 9 Drawing Sheets

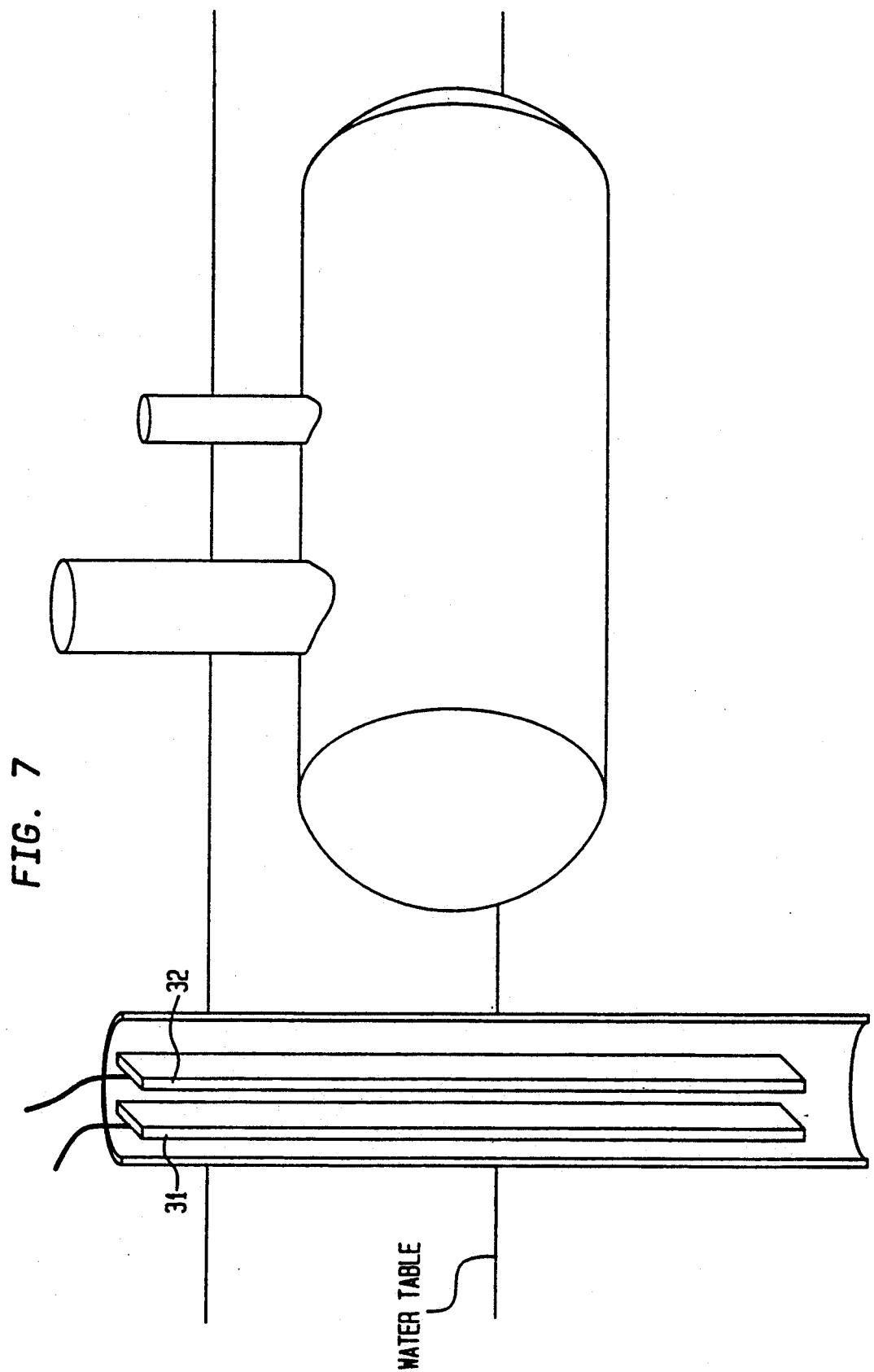

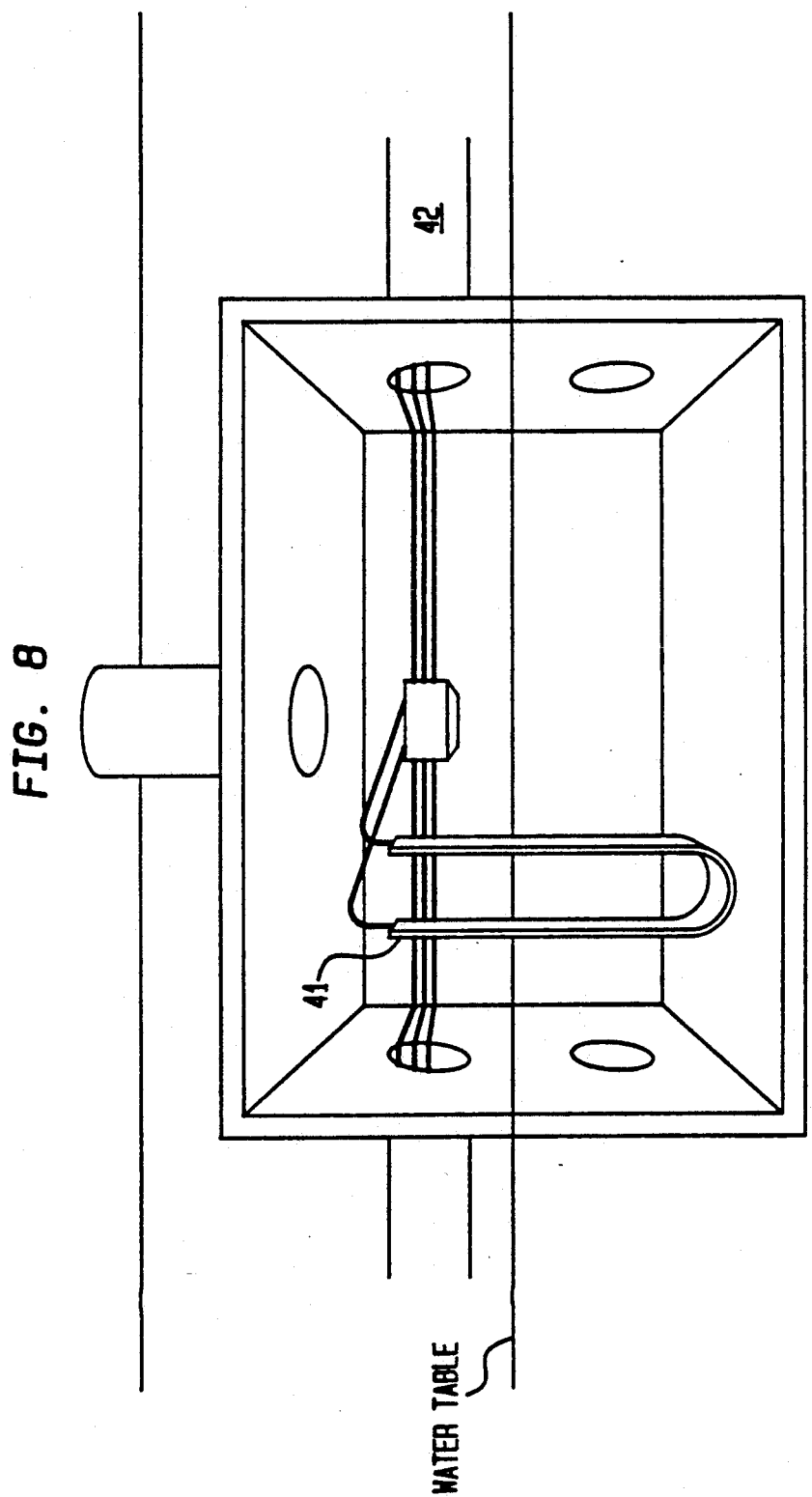

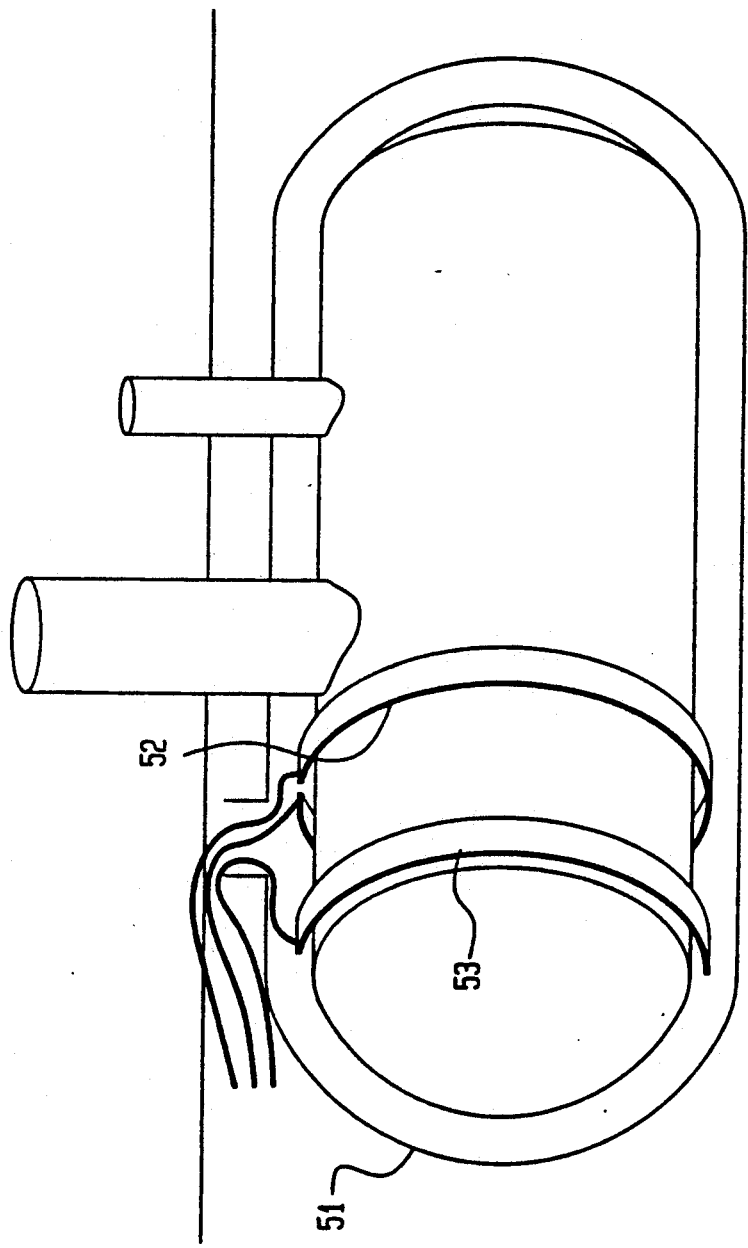

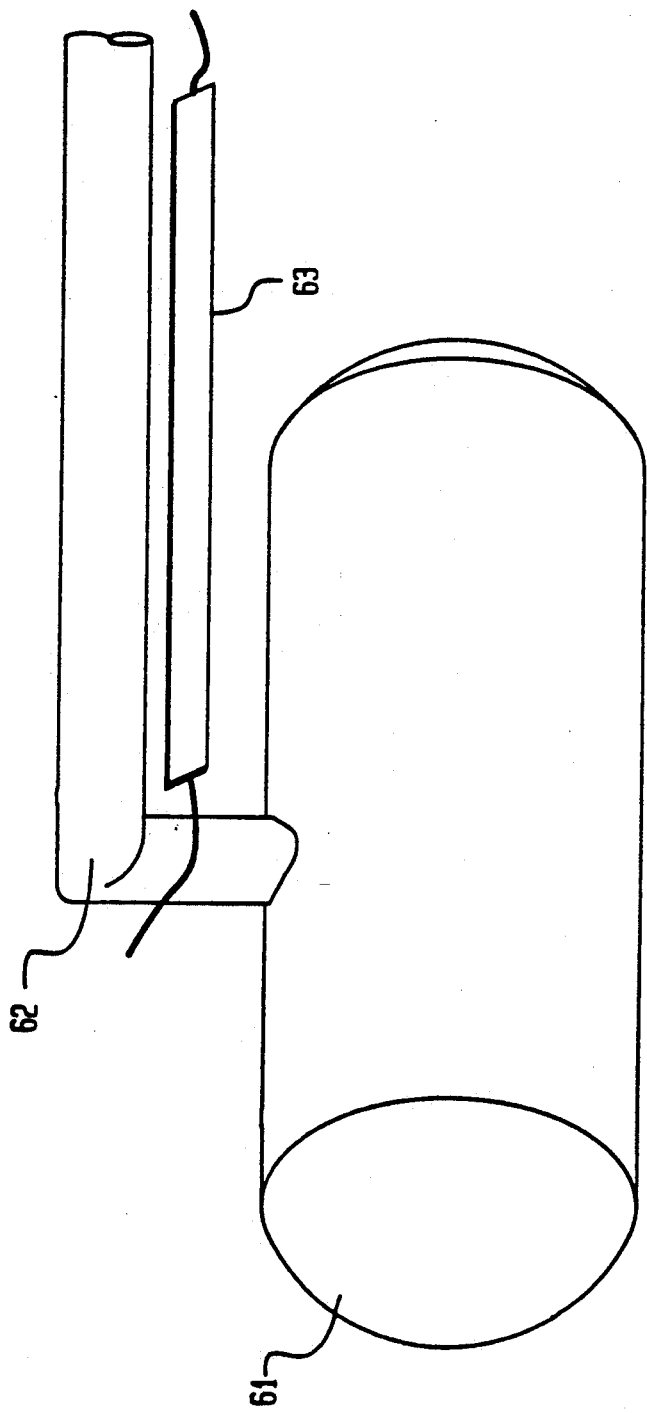

METHOD FOR SELECTIVE DETECTION OF LIQUID PHASE HYDROCARBONS

RELATED APPLICATION

This application is a division of application Ser. No. 07/584,894, filed Sept. 20, 1990, which is a continuation-in-part of application Ser. No. 07/371,542, fled Jun. 26, 1989, now abandoned.

FIELD OF THE INVENTION

This invention relates to a transducer for sensing liquid phase chemical pollutants. More particularly, the present invention relates to a chemically actuated electronic switch comprising a conductive polymer tape suitable for the selective detection of liquid phase hydrocarbons at any point along its length.

BACKGROUND OF THE INVENTION

In the current oil-driven economy, vast amounts of petroleum fuels are stored in holding tanks, the majority of such tanks being located underground. These installations provide an economic alternative to aboveground installations and result in a significant reduction in the risk of fire or explosions. Underground storage tanks installed prior to 1985 were usually constructed of steel with only minimal protection from corrosion. Furthermore, few of these tanks were fitted with means for detecting leaks of stored fuel. Unfortunately, these factors have contributed to the undetected contamination of adjacent soil and aquifer.

In response to the problems created by leakage of such underground storage tanks, the United States Environmental Protection Agency recently sponsored legislation, placing financial responsibility for any such leakage upon the owners and operators of such tanks. Initially, underground storage tank owners and operators were required to register commercial tanks, so providing an index as to the number and size of the tanks present in the United States. Approximately 3,000,000 tanks were registered in response to this requirement. Thereafter, the Agency published additional regulations which required retrofitting commercial tanks with release monitoring systems including a means for the detection of hydrocarbon fuel seepage into the environment and also requiring the maintenance of liability insurance in the event of actual leakage.

Accordingly, there has been widespread interest in the industrial community for the development of suitable detectors capable of sensing leakage of liquid hydrocarbon fuels from underground storage tanks. Among the many industries feeling the impact of such regulations is the telephone industry which collectively maintains in excess of 20,000 storage tanks which are used to store diesel fuel for central office emergency power, fuel oil to heat buildings and gasoline for vehicle fleets. Although some of these tanks are currently exempt from the Federal requirements, it is anticipated that legislation at both the Federal and State levels will eventually require leak detection equipment on all such tanks. Additionally, hydrocarbon fuels such as gasoline, kerosene or diesel fuel present in the soil or floating on the water table can infiltrate underground telephone cable ducts and drain into utility holes. Failure to promptly remove these contaminants may result in irreversible damage to the seals on exposed cables or splice cases, so permitting water to enter the cable core or splice case, which results in the short circuiting of the conductors and necessitates expensive repair or replacement.

Heretofore, a wide variety of leak detectors have been proposed for this purpose. Among such detectors are mechanical float devices, thermal conductivity detectors, metal oxide semiconductors and conductive rubber materials. Each of these devices has certain advantages and limitations. However, the conductive rubbers are potentially the most attractive because they are generally durable, relatively inexpensive and exhibit a significant increase in resistance in the presence of non-polar organic materials such as the hydrocarbon fuels. In practice, however, they have not emerged as the optimum underground fuel sensor design because, up to now, their disadvantages have outweighed their advantages.

All of these conductive rubber detectors are based upon insulating plastic or rubber materials which comprise conductive bodies, such as carbon black or metallic particles, sufficient to yield a semiconductive composite. Upon contact with hydrocarbon liquid and/or vapors, the resistance of the composite increases dramatically. Thus, for example, U.S. Pat. No. 2,691,134 issued to C. S. Ford on Oct. 5, 1954 relates to a device for detecting the leakage of inflammable fluids such as gasoline, gasoline vapors and the like from storage receptacles. The patentee describes a sensor comprising an electrically conductive rubber having an initial resistance which increases dramatically upon contact with hydrocarbon fuel. Upon removal of the fluid, the initial resistance of the conductive material is restored.

Following this invention, several carbon black/rubber composites were described in the patent literature, each optimizing a particular aspect of the aforementioned Ford patent. Thus, for example, U.S. Pat. No. 3,045,198 issued to J. P. Dolan and William N. Jordan on Jul. 17, 1962 relates to a detection device based upon the concept of adsorption of hydrocarbon vapors on exposed carbon black particles adhered to a rigid substrate with a silicone rubber adhesive. In the presence of hydrocarbon vapors, the resistance of this device increases dramatically. Further modifications to this device were described in later patents issued to Dolan, namely, U.S. Pat. Nos. 4,129,030, 4,224,595, and 4,237,721. There are, however, practical drawbacks to the Dolan devices. Initially, it is noted that these devices are useful for sensing only hydrocarbon vapors and will not tolerate continuous contact with liquid hydrocarbons or water. Furthermore, these sensors are not rugged, cannot be submerged and require a rigid substrate. Accordingly, the Dolan sensors must be discarded after use and are useful only as point sensors, so limiting their applicability for commercial detection. Still further, the large carbon particles employed tend to fall out of the silicone adhesive with the passage of time, so causing the resistance to change.

An alternative device for detection of hydrocarbon fuels is described in U.S. Pat. No. 4,631,952 issued on Dec. 30, 1986 to L. F. Donaghey. This device comprises a conductive rubber sensor which is capable of detecting hydrocarbons in both the liquid and vapor state. The sensor includes spherical carbon particles dispersed homogeneously in a silicone rubber matrix. This composite is similar to the Dolan devices in that when contacted with liquid or gaseous hydrocarbons the resistance increases substantially presumably because of the swelling of the silicone matrix and/or adsorption of liquid on the carbon particle surface. In light of the fact that this composite is a homogeneous mixture of carbon particles and silicone, it is an enhancement of the Dolan device in that it functions in the presence of liquids and gases and is completely reversible. Additionally, it is easy to fabricate since dispersion of the conductive filler in the polymer is effected using conventional plastic or rubber mixing equipment. However, the Donaghey device does have two major limitations which makes it impractical as a device for detecting the presence of fuel in a variety of applications. The first limitation occurs because the sensor is so sensitive to hydrocarbon vapors that it continually gives rise to false alarms in areas where there may be no more than traces of hydrocarbon fuel spills even though they had been previously removed. Furthermore, many of the new tanks being installed underground are of the double wall variety. As such, the concentration of fuel vapor can be high in the annular space as a result of diffusion through fiberglass or seepage through welding points, so causing the device to trigger an alarm even though there was no liquid leak. The second limitation arises from the high carbon black concentration which causes a severe reduction in mechanical strength and thereby limits the use for distributed sensing applications.

Interestingly, one of the limitations of the Donaghey device was addressed in U.S. Pat. No. 4,855,706 issued to P. D. Hauptly on Aug. 8, 1989. The Hauptly device detects only liquid hydrocarbons and not interfering vapors. Analysis of the patent reveals that it is essentially the same as the Donaghey device but for the fact that the carbon concentration is much higher, namely, in the range of 78-97 weight percent. Due to the fact that the swellable polymer concentration is so small, only liquid hydrocarbons enlarge the material sufficiently to cause a significant increase in resistance. Unfortunately, this approach is unsatisfactory since the sensor material is very brittle, and like the Dolan devices, requires a rigid substrate with a defined shape. Thus, this device is only feasible for applications which utilize point sensing rather than distributed sensors.

SUMMARY OF THE INVENTION

In accordance with the present invention, the prior art limitations alluded to hereinabove have been obviated by means of a novel electrical transducer which is highly sensitive to liquid hydrocarbons but only slightly sensitive to hydrocarbon vapors. The sensor comprises from 10-30 weight percent of a small particle size, high structure carbon black homogeneously dispersed in a silicone matrix. This sensor, in the same fashion of other conductive rubber sensors, is normally conductive but switches to a high resistance state when contacted with and swollen by liquid hydrocarbons.

Due to the low carbon black concentration and unlike the Donaghey or Hauptly devices, the sensor is capable of being fabricated in strong, flexible conductive tapes ranging in length up to several thousand feet. The tape so fabricated is capable of sensing liquid hydrocarbon fuels at any point along its length and is superior to those devices which can only be fabricated in short lengths or defined geometries. The tape may also be hung vertically in a sensory well or strapped horizontally to a pipe connecting a tank to a pump. In light of the fact that the sensor does not respond to background hydrocarbon vapors, it overcomes the problem of triggering false alarms. The described sensors are completely reversible and need not be replaced after contact with liquid gasoline, the volatile fuel simply evaporating and resulting in a decrease of resistance to its original dry value. (Less volatile fuels such as kerosene or diesel fuel may be removed easily by washing the contaminated area of the sensor with gasoline, followed by evaporation of the gasoline.) The reversibility of the sensor permits frequent checking of the entire system, so obviating the need to discard the tested sensor and the ambiguity of operation which arises upon installation of a new sensor.

Studies have revealed that the described sensor is capable of detecting nearly all common liquid hydrocarbon fuels including gasoline, kerosene, No. 1 and No. 2 fuel oil, jet fuel and diesel fuel (but not heavier oils such as motor oil or mineral oil) with a response time varying from less than a minute up to about an hour dependent upon the viscosity of the fuel and the thickness of the tape. Activation typically results in an increase of electrical resistance by greater than ten orders of magnitude. As further evidence of the selectivity of the sensor, it has been found to be non-responsive to water, slightly responsive to alcohols and provides an intermediate response to materials of intermediate polarity such as chloroform, acetone, or cleaning fluids.

The invention will be more readily understood by reference to the following detailed description taken in conjunction with the accompanying drawing wherein:

FIG. 7 is a front elevational view in cross section of an underground fuel storage tank together with a fuel sensor which becomes disabled when the water table falls below the sensor length;

FIG. 8 is a front elevational view in cross section of a sensor of the invention mounted in a utility hole installation;

FIG. 9 is a front elevational view in cross section of a double walled underground storage tank adapted with the sensor of the invention in the interstitial space; and FIG. 10 is a front elevational view in cross section of an underground fuel storage tank adapted with external piping and having a fuel sensor of the invention in proximity thereto.

DESCRIPTION OF THE INVENTION

Figure 1:
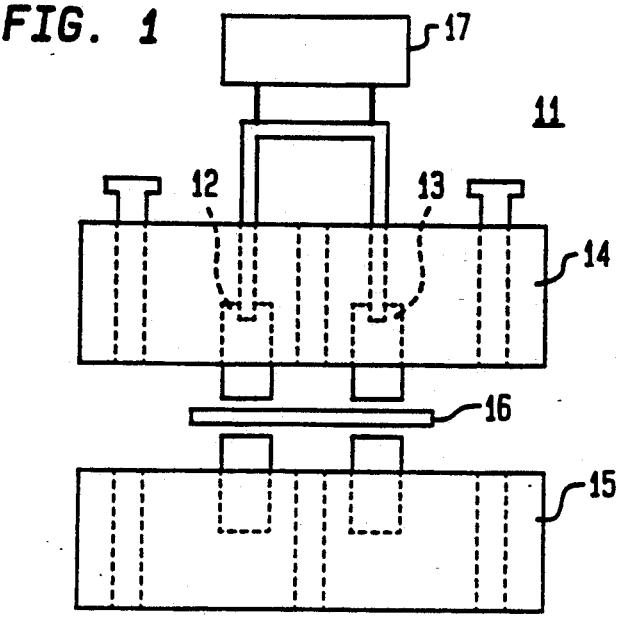
FIG. 1 is a plan view of the liquid phase sensor of the invention as mounted in a typical measurement apparatus.

With reference now to FIG. 1, there is shown a plan view of the sensor of the invention as mounted in a typical measurement apparatus. Shown is a pressure block cell 11 suitable for measuring the resistance across the length of the thin film composite. This cell is comprised of a pair of electrical contacts 12 and 13 mounted in a polytetrafluoroethylene block 14 with an opposite block 15 of similar design to ensure good electrical contact to the composite 16. Means 17 is employed to measure the resistance of the composite.

Figure 2:
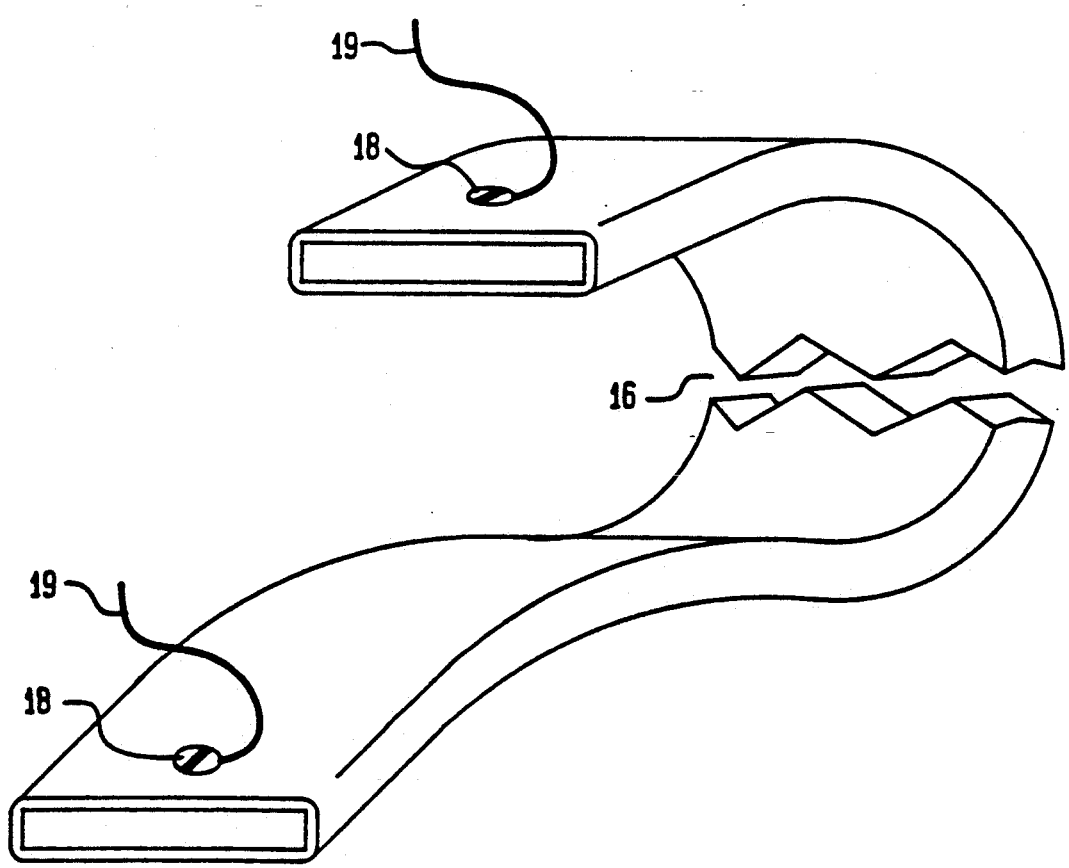
FIG. 2 is a three-dimensional view of the sensor of the invention.

Shown in FIG. 2 is a three dimensional view of a typical sensor of the invention 16 having screw contacts 18 to which are connected leads 19 from a resistance measuring source (not shown). The elastomer selected for use in the practice of the invention is chosen from among the silicone polymers or rubbers, or other elastomeric materials, which swell in the presence of liquid hydrocarbons. When contacted by liquid hydrocarbons, swelling of the polymer occurs, so causing a change in electronic state from conductive to insulating when the appropriate conductive filler is employed. The liquid hydrocarbons alluded to include crude oil fractions in the $C_6$ to $C_{16}$ range which correspond with commercial fuel fractions, such as gasoline, kerosene, diesel fuel, jet fuel and the like.

The filler selected for use in the practice of the invention is a conductive carbon black of high structure having an average particle size ranging from 10 to 50 millimicrons. The structure of carbon black is a measure of the amount of "chaining" of the black primary aggregates and is directly related to the oil absorption measurement (cc dibutylphthalate/100g black). For the purposes of the present invention, the high structure black evidences an oil absorption measurement greater than 150. Additionally, the high structure black must evidence less than 2 percent volatiles (oxygen on surface). Thus, a significant aspect of the present invention resides in the discovery that structure of the carbon black is critical in fuel sensing applications, that is, whether the carbon black is a "low structure" or a "high structure" black. The low structure blacks tend to disperse in polymeric media as spherical, slightly agglomerated particles. High structure blacks, in marked contrast therewith, tend to disperse as highly agglomerated chains and are more conductive at a defined carbon black concentration. It has been determined that, given a similar particle size, fuel sensors made from high structure blacks are vastly different from those formulated from low structure blacks. Specifically, the high structure black composites are much more phase selective, that is, respond to liquid but not to vapors, than low structure composites. Furthermore, the former require approximately one-half the amount of carbon to attain the same conductivity as the latter. In order to illustrate this point, the composite described in U.S. Pat. No. 4,631,952, hereinabove was compared with the composite used in the sensor described herein. Both the patented sensor and the sensor of the invention comprise carbon black particles dispersed in dimethyl silicone rubber. However, the patented composite is comprised of "low structure" carbon particles, resulting in a markedly different sensor. In fact, three major departures are identified.

First, it is noted that the prior art sensor incorporates very large concentrations of carbon black, ranging from 1:4 to 4:1 (conductive material to swellable material) with an optimum range corresponding to the 1:1 to 2:1 materials. These ratios correspond with a range of 20-80 weight percent carbon black concentration in dimethyl silicone rubber or 50-67 weight percent carbon black for the specified optimum range. Analysis of the reference reveals that the patentee employed a 2:1 carbon black/silicone rubber ratio in the exemplary embodiments. In making the comparison, however, a 1:1 ratio was employed to permit the most favorable comparison with the material of the invention since this ratio yields the least brittle of the formulations in the optimum 1:1 to 2:1 range.

Figure 3:
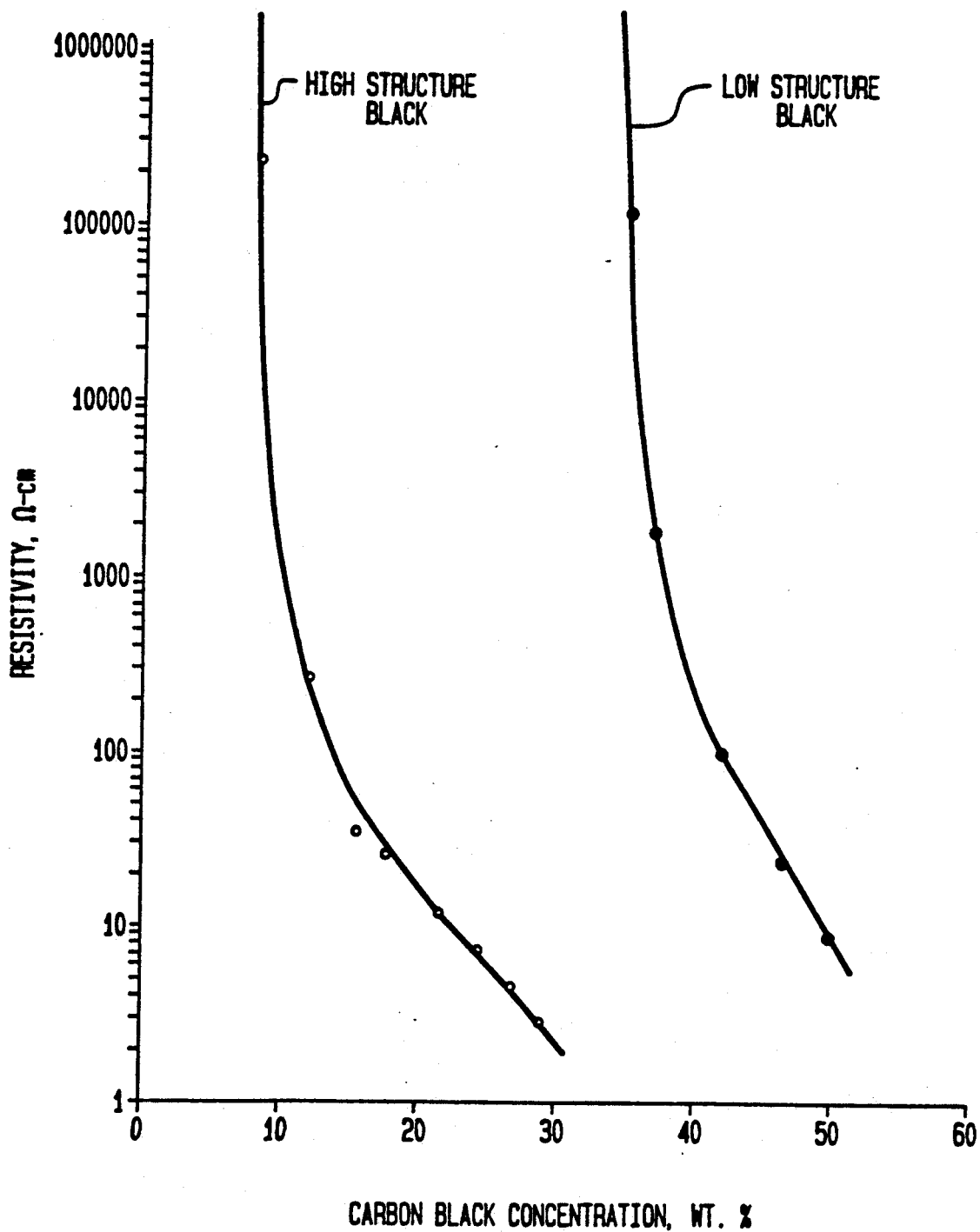
FIG. 3 is a graphical representation on coordinates of carbon black concentration in weight percent against resistivity in ohm-cm showing the response of a conductive silicone rubber matrix to liquid hydrocarbons for a matrix containing a low structure carbon black of the prior art and a high structure carbon black of the invention.

With reference now to FIG. 3 there is shown a graphical representation on coordinates of carbon black concentration in weight percent against resistivity in ohm-cm comparing the resistivity of the above-noted prior art sensor with the described sensor at various carbon black concentrations. It is apparent by reference to the curves that more than twice as much black is required for the low structure black to attain the same conductivity as the high structure material. It should also be noted that the low structure composite is no longer conductive and, therefore, no longer capable of acting as a fuel sensor at carbon black concentrations of less than 30 weight percent. However, the sensor described herein continues to sense fuel down to 10 weight percent carbon black although the optimum formulation is within the range of 20-30 weight percent black.

Figure 4:
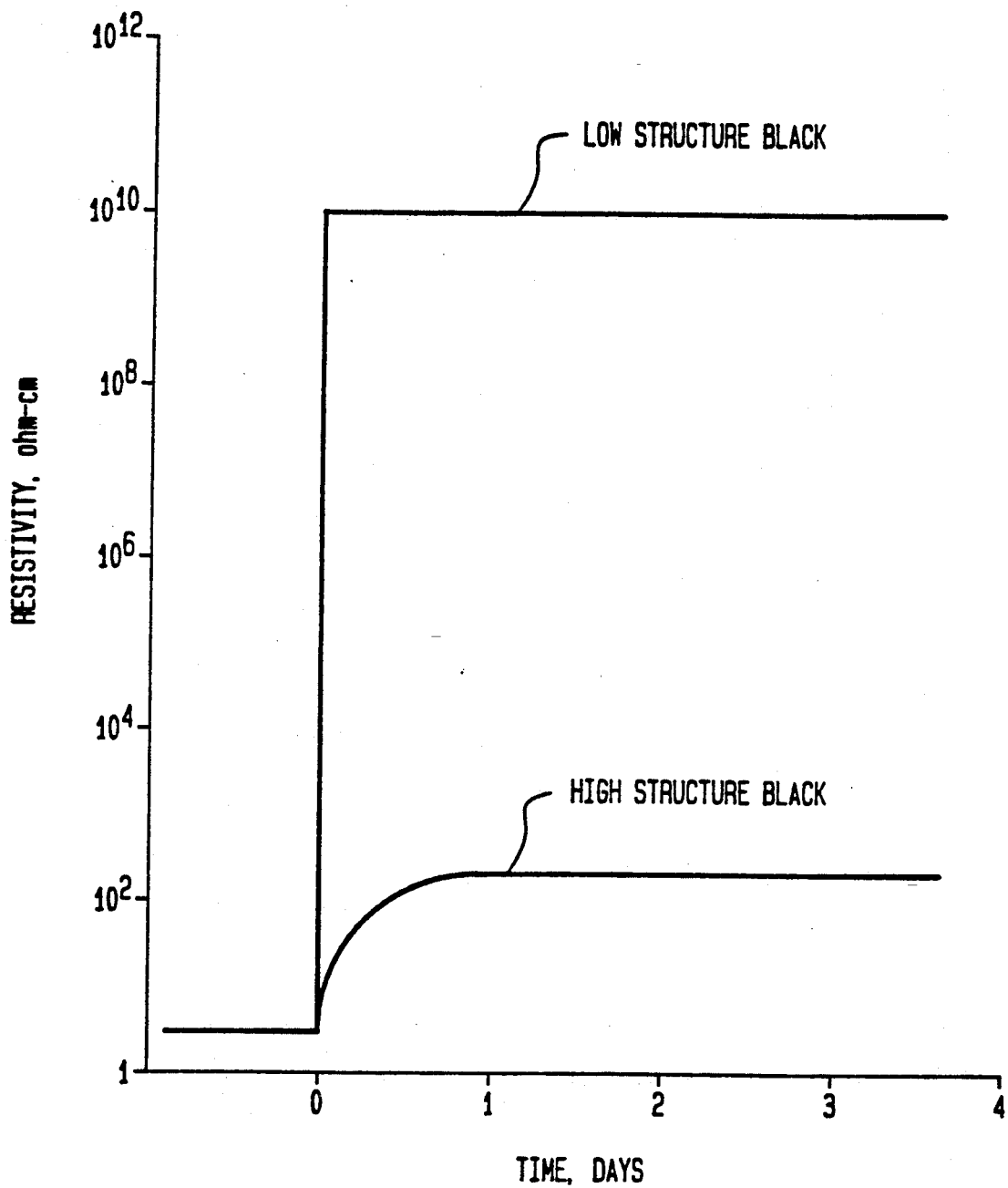
FIG. 4 is a graphical representation on coordinates of time in days against resistivity in ohm-cm showing a comparison of the response of the sensors alluded to in FIG. 3 to gasoline vapor at room temperature.

The second distinction is noted by reference to FIG. 4, wherein there is shown a graphical representation on coordinates of time in days against resistivity in ohm-cm, comparing the gasoline vapor sensing properties of the low structure and high structure carbon black/silicone rubber composite described in FIG. 3. Each of the composites was placed in a closed volume in the space over liquid gasoline with the resistivity monitored as a function of time. Data was compiled using the apparatus shown in FIG. 6. It is noted that the low structure prior art composite in a matter of minutes has switched to a very high resistance, so signifying the presence of fuel vapor. The high structure composite of the invention reveals that while the resistance has increased, it has changed by less than two orders of magnitude for vaporous fuel as compared to ten orders of magnitude for the prior art. Consequently, the high structure carbon composite can be used for the exclusive detection of liquid hydrocarbons. In summation, it may then be concluded that the low structure carbon of the prior art sensor behaves as a vapor and liquid sensor, as stated in the prior art but the high structure carbon sensor behaves primarily as a liquid sensor which is essentially or partially insensitive to background vapor, so fulfilling an industry requirement.

Examination of the two curves shown in FIG. 3 reveals why the response to hydrocarbon vapors is so different for the low structure and high structure carbon black/silicone rubber fuel sensor materials. When gasoline vapor swells the silicone to a larger volume, the original carbon black concentration is reduced proportionately. For illustrative purposes, if the silicone fraction in the 50 weight percent low structure composite is swollen with gasoline vapor to twice its original volume, the effective black concentration is reduced to about 33 weight percent black. At that concentration, reference to the FIGURE reveals that the low structure black composite has already switched to the insulating state. However, in the case of an initially equally conductive high structure black composite, a 25 weight percent black material effectively becomes 14 weight percent black after exposure and equilibration with the same gasoline vapor. Again, with reference to the FIGURE, it will be noted that the 14 weight percent high structure black composite is still conductive since it has not switched to the insulating state. In the case of contact with liquid hydrocarbons, both composites increase sufficiently in volume to switch to the insulating state.

Figure 5:
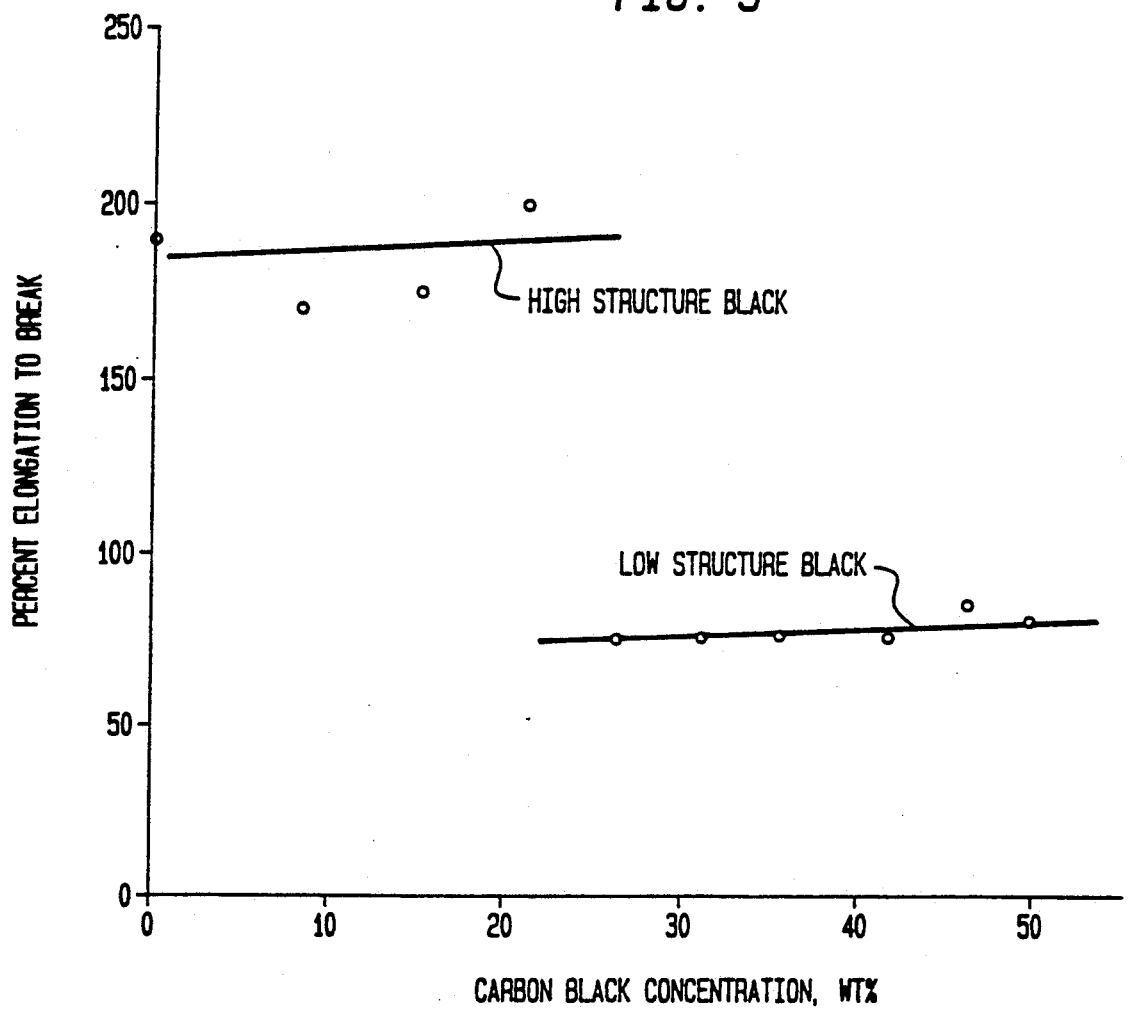
FIG. 5 is a graphical representation on coordinates of carbon black concentration against percent elongation showing a comparison between elongation characteristics of the sensor of the invention and a typical prior art sensor.

Third, a further requirement of the distributed sensor of the invention is that it be of high mechanical strength. The low concentration of carbon black in the high structure carbon black silicone composite is advantageous in that mechanical strength is not seriously compromised. Thus, in FIG. 5 which is a graphical representation on coordinates of carbon black concentration in weight percent against percent elongation, a comparison is made of percent elongation-to-break of low structure and high structure carbon black composite fuel sensors. It is evident that the low structure black results in a relatively weak material with elongations of between 50 and 100 percent. It is well known in the industry that long, thin, flexible polymer structures such as wire insulations, cable jackets and hose materials must have elongations significantly greater than 100 percent to be self-supporting and survive the kinks, twists and other forms of handling encountered in industrial applications. Furthermore, the carbon black/silicone rubber composite elongations plotted in FIG. 5 (1:1 carbon black/silicone) are the most flexible in the optimum range claimed by the prior art. Since they represent the low end of the specified low structure black concentration range, higher concentrations of carbon black result in materials with even lower elongations than those noted in the FIGURE.

In marked comparison, the high structure black materials evidence elongation properties of greater than 150 percent, thus meeting minimum requirements with ample reserve. This characteristic permits the formulation of tough, durable sensing tapes that can be handled roughly without concern for breakage, either during installation or thereafter in the underground environment. In contrast thereto, the limited elongations of the low structure materials preclude their use as reliable, rugged distributed sensors.

The described fuel sensor of the invention may be prepared by blending a "high structure", small particle size carbon black in a two part silicone elastomer and, subsequently, extruding the resultant composition into a tape which is cured by the application of heat. In a typical procedure, curing is effected at 150° C. for 15 minutes. An additional extrusion may be necessary to insulate the tape with a clear non-conducting silicone. This insulating procedure may also occur simultaneously with the original tape extrusion, or it may be applied and cured in a subsequent step.

In a specific embodiment, 4 parts of a commercially available high structure black were blended with 11 parts of dimethyl silicone encapsulant, so resulting in a blend containing 26.7 weight percent black. The viscous mixture was then either compression molded or extruded and cured at 150° C. for 15 minutes. The resistivity of the final material was 4 ohm-cm. Accordingly, a tape about 0.8 mm thick, 12.5 mm wide, and 6 metres in length would have an initial resistance of about 25,000 ohms.

Figure 6:
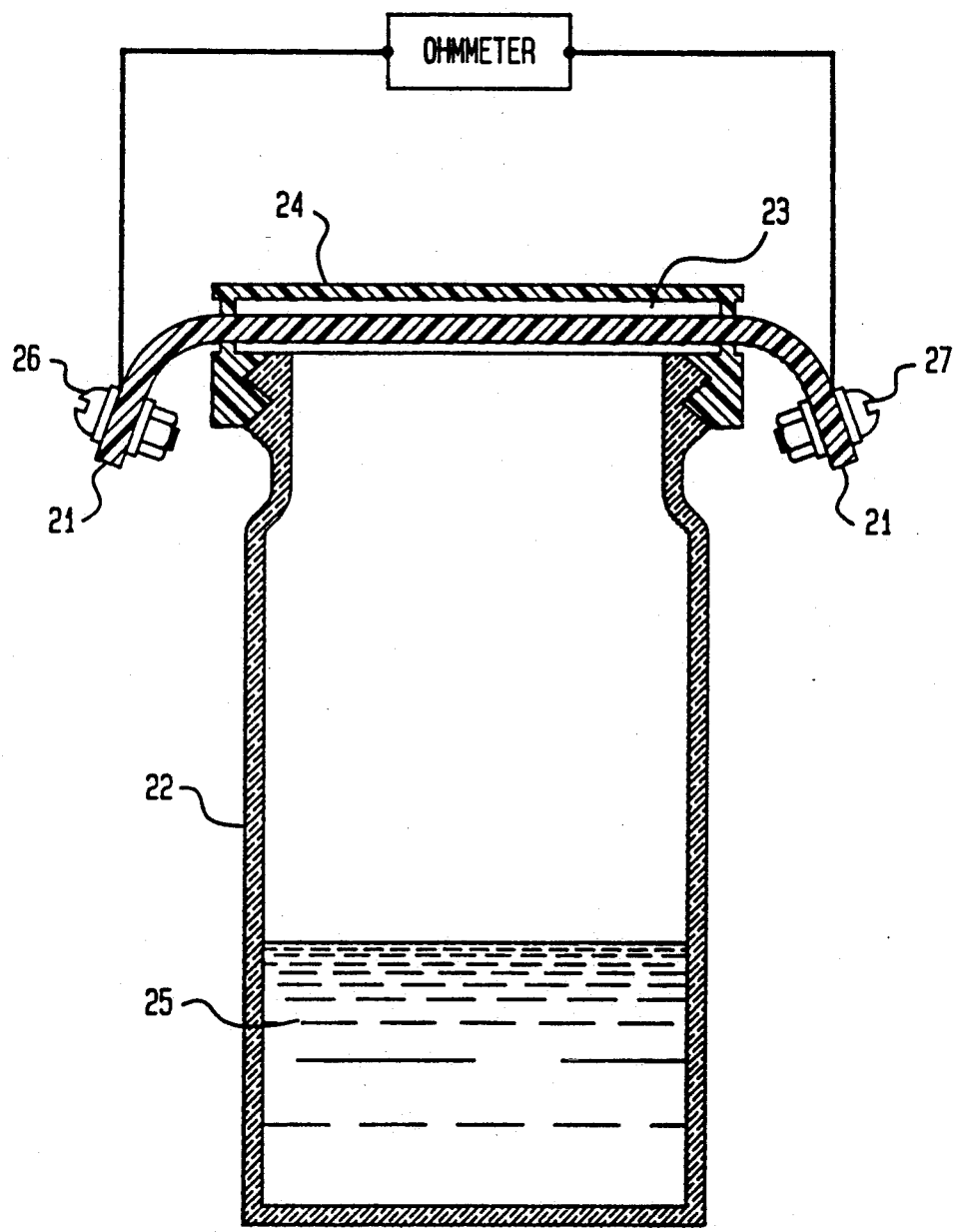
FIG. 6 is a front elevational view of a glass jar containing a hydrocarbon in liquid form, the jar being adapted with the sensor of the invention.

FIG. 6 is a front elevational view of a glass jar which was used to measure the resistance of various samples in the vapor state. Tapes of carbon black/silicone composites fabricated in thicknesses from about 0.25 to 0.8 mm and lengths of about 75 mm were used. Sensor 21 was mounted in jar 22 adapted with gasket 23 and cap 24 containing a liquid fuel 25 and equilibrated and measured first in the vapor above the liquid and then tipped upside down and measured in the liquid. Electrical connections to tape 21 were made outside the jar with simple screw connections 26 and 27.

To determine the efficacy of the described transducer for hydrocarbon sensing, using the apparatus in FIG. 6 the composite was immersed in a wide variety of solvents as well as high molecular weight mineral oils representative of those oils commonly used in combustion engines for lubrication. In those cases where the solvent acts as a swelling agent for the silicone polymer, the effective conductive carbon black concentration is reduced, thereby causing a corresponding increase in resistance. With reference now the Table, resistivity data have been tabulated for immersion of a 0.8 mm thick film of 24 wt. % carbon black composite into the solvents noted. In the Table, $p_i$ and $p_f$ are the initial and final resistivities before and after immersion in solvent.

A measure of the ability of the sensor to detect a given solvent can be represented by the quantity $\log(p_f/p_i)$. For instance, a weak solvent-polymer interaction is exemplified by little or no swelling of the silicone, resulting in values for $\log(p_f/p_i)$ of $<2$. Highly polar materials such as water and alcohols are examples of solvents in this first category. Thus water, the most common and natural underground liquid substance, does not interfere with the measurement.

The intermediate regime will exhibit moderate swelling, giving values of $\log(p_f/p_i)$ of 2-6; here typical solvents include the halogenated organics such as methylene chloride, chloroform, trichloroethane, and typical cleaning fluids. These materials may or may not switch the sensor when they come into contact with the element, depending on the threshold resistance in the associated electronics. Since the halocarbons are all heavier than water, however, they might never come into contact with the sensing element in the underground environment because they would sink to the bottom of the aquifer.

Finally, the strongest interactions will expand the silicone polymer volume the most, and $p_f/p_i$ will take on values of $>6$. Low molecular liquid alkanes and alkenes, such as hexane, octane, decane, dodecane and hexadecane, as well as all common hydrocarbon fuels, fall into this last category. Higher molecular weight lubricating or paraffin oils, however, will not swell the silicone material and, accordingly, will not switch the composite from the conductive to the nonconductive state.

Again referring to the Table, $p_r$ is defined as the volume resistivity of the composite high structure sensor after immersion in solvent followed by complete extraction or evaporation of solvent. Thus, to determine the chemical and electrical reversibility of this sensor, a 24 wt. % high structure carbon black composite film was immersed repeatedly into the solvents designated in the Table followed by complete solvent evaporation. The near zero values of the quantity $\log(p_r/p_i)$ dictate that upon contact with all solvents so indicated the sensor returns to its initial chemical and electrical states. Such performance allows testing of the sensor without loss in functionality and reliability.

TABLE

| Solvent | log $(\rho_f/\rho_i)$ | log $(\rho_r/\rho_i)$ |
| --- | --- | --- |
| hexane | 9.44 | −0.11 |
| octane | 9.67 | −0.10 |
| decane | 9.47 | −0.40 |
| dodecane | 10.2 | −0.17 |
| tetradecane | 9.97 | −0.05 |
| hexadecane | 6.97 | −0.26 |
| dichloromethane | 5.27 | −0.23 |
| 1,2-dichloroethane | 2.36 | −0.19 |
| 1,1,1-trichloroethane | 6.58 | −0.21 |
| Freon TF[a] | 10.6 | −0.20 |
| methanol | −0.05 | −0.18 |
| ethanol | 0.42 | −0.03 |
| 1-octanol | 0.94 | −0.06 |
| ethylene glycol | 0.01 | −0.07 |
| benzene | 9.20 | −0.26 |
| toluene | 9.23 | −0.24 |
| diethyl ether | 7.47 | −0.17 |
| chloroform | 6.15 | −0.24 |
| acetonitrile | 0.06 | −0.03 |
| acetone | 1.51 | −0.14 |
| tetrahydrofuran | 5.99 | −0.16 |
| ethyl acetate | 5.92 | −0.17 |
| water (18 MΩ-cm) | −0.03 | −0.08 |
| Oil standard S20 | 1.20 | 0.01 |
| Oil standard S60 | 0.58 | 0.0 |
| Oil standard S200 | 0.33 | 0.0 |
| Oil standard S600 | 0.18 | 0.0 |

[a]Chemical formula $CF_2ClCFCl_2$

The versatility of the sensor of the invention will be appreciated by the following illustration. In order to verify the presence of water at depths less than about 6 metres as required by U.S. Environmental Protection Agency tank regulation, a sensor configuration may be employed which uses the ground water as a circuit element. In this configuration shown in FIG. 7, two separate 6 metre vertical lengths 31 and 32 of the sensor of the invention are placed in a monitoring well. In the presence of water, the configuration behaves as a low resistance circuit with water completing the current between sensor 31 and 32. When the water table falls below about 6 metres, however, now current will flow in the external circuit. Thus, an open circuit indicates either (1) that liquid fuel is present in the monitoring well (presumably a fuel leak), or (2) that the water table has dropped below the Federal requirements of being within about 6 metres of grade to permit use of release detection techniques that sense fuel on top of the water table, or (3) the external circuit has been broken. In any event, the incident will prompt an investigation on the site.

A still further application for the described sensor is in utility holes which are unique in that they are generally located at distances up to several miles from a telephone central office housing a monitoring system. Additionally, utility holes may be susceptible to the intrusion or deliberate dumping of chemicals. Because the electrical connections must be made in the utility hole, care must be taken to isolate external electrical connections from the environment and to avoid corrosion. FIG. 8 illustrates this configuration, showing continuous looped electrically insulated coated sensor 41 which is installed vertically so that fuel in utility hole 42 floating on the water table at any height will cause a high resistance condition at that point. Allowance is made for the fact that only liquid hydrocarbons will cause damage to the underground plant and that a residual volume of water is almost always present in a utility hole.

For interstitial monitoring, it is not only important to detect leakage of fuel through the primary containment barrier, but it is also critical to detect the presence of water in the annular space (of a double-walled tank) since this may indicate a rupture in the secondary containment barrier. In the remote case in which both liquids are present, a fuel leak will take precedence, and the sensor's response will not be masked by the presence of water. In FIG. 9, there is shown underground double-walled storage tank 51 having a sensor tape 52 of the invention disposed thereabout in the interstitial space between the two walls of the tank. The intrusion of water into the annular space causes the detection circuit current to short circuit to the ground lead 53 in the detection circuit (not shown) to drop to a level much less than the resistance at which the circuit idles. The presence of fuel will cause an open circuit condition notwithstanding the presence of water.

Further, a sensor can also be placed in proximity to the exit piping from the underground storage tank. In FIG. 10, an underground storage tank 61 adapted with exit pipe 62 is shown. In proximity to the exit pipe, sensor 63 is positioned. In this manner, fuel leaks along the piping may be sensed and a long sensor length is ideal for this purpose.

While the invention has been described in detail in the foregoing specification, it will be understood by those skilled in the art that variations may be made without departing from the spirit and scope of the invention.

What is claimed is:

1. A method for selectively distinguishing the presence of the liquid phase of a hydrocarbon in an environment containing the vapor phase of said hydrocarbon, said method comprising:
   a) providing a sensor consisting essentially of a normally electrically conductive blend of a silicone polymer and a high structure carbon black of fine particle size, said carbon black being present in an amount ranging from 10–30 weight percent based on the weight of said blend;
   b) determining the electrical resistivity of said sensor when in contact with said hydrocarbon vapor phase;
   c) determining the electrical resistivity of said sensor when in contact with said hydrocarbon liquid phase;
   d) disposing said sensor in said environment in a manner which will ensure contact with any liquid phase of said hydrocarbon that may enter said environment;
   e) monitoring the electrical resistivity of said sensor; and
   f) signaling the presence of said hydrocarbon liquid phase when the electrical resistivity of said sensor increases to a preselected threshold level intermediate said vapor phase and liquid phase resistivities.

* * * * *